United States Patent

Kohl et al.

[11] Patent Number: 5,825,488
[45] Date of Patent: Oct. 20, 1998

[54] METHOD AND APPARATUS FOR DETERMINING ANALYTICAL DATA CONCERNING THE INSIDE OF A SCATTERING MATRIX

[75] Inventors: Matthias Kohl, London; Mark Cope, Avon, both of Great Britain; Matthias Essenpreis, Gauting; Dirk Boecker, Heidelberg, both of Germany

[73] Assignee: Boehringer Mannheim GmbH, Mannheim, Germany

[21] Appl. No.: 745,204

[22] Filed: Nov. 8, 1996

[30] Foreign Application Priority Data

Nov. 18, 1995 [DE] Germany .................. 195 43 020.4

[51] Int. Cl.$^6$ .................................................. G01N 21/47
[52] U.S. Cl. ........................................... 356/342; 128/633
[58] Field of Search ................................... 356/336, 337, 356/342; 128/633, 634, 665

[56] References Cited

U.S. PATENT DOCUMENTS

| | | | |
|---|---|---|---|
| 4,555,179 | 11/1985 | Langerholc et al. | 356/237 |
| 5,057,695 | 10/1991 | Hirao et al. | 250/575 |
| 5,137,355 | 8/1992 | Barbour et al. | 356/342 |
| 5,284,149 | 2/1994 | Dhadwal et al. | 128/665 |
| 5,285,783 | 2/1994 | Secker | 128/633 |
| 5,517,987 | 5/1996 | Tsuchiya | 128/633 |
| 5,596,987 | 1/1997 | Chance | 128/633 |
| 5,636,637 | 6/1997 | Guiolet et al. | 128/665 |

FOREIGN PATENT DOCUMENTS

| | | |
|---|---|---|
| 43 14 835 | 11/1994 | Germany . |
| 44 14 679 | 11/1995 | Germany . |
| 44 17 639 | 11/1995 | Germany . |

OTHER PUBLICATIONS

Brenci et al., Sensors and Actuators, "An optial–fiber sensor for the measurement of the size and density of monodisperse particulates", (1995) 23–27 (no month available).

Keijzer et al., Applied Optics, "Optical diffusion in layered media", vol. 27, No. 9, 1 May 1988.

Flock et al, IEEE, "Monte Carlo Modeling of Light Propagation in Highly Scattering Tissues. . . .", vol. 36, No. 12, Dec. 1989.

Farrell et al, Med. Phys., "A diffusion theory model of spatially resolved, steady–state diffuse. . . .", 19 (4) Jul./Aug. 1992.

*Primary Examiner*—Frank G. Font
*Assistant Examiner*—Zandra V. Smith
*Attorney, Agent, or Firm*—Nikaido, Marmelstein, Murray & Oram LLP

[57] ABSTRACT

A method and an apparatus for determining analytical data concerning the inside of a scattering matrix, in particular of a biological sample. In a detection step detection measurements are carried out in which light is irradiated into the matrix as primary light at an irradiation site (12) through an interface bounding the scattering matrix (6) and light emerging out of the scattering matrix through the interface is detected as secondary light at a detection site (13) at a predetermined measuring distance from the irradiation site, in order to determine as a measurement variable a measurable physical property of the light which varies due to the interaction of the light with the scattering matrix, which measurement variable is a measure of the analytical data to be determined. In an evaluation step the analytical data are determined on the basis of the measurement variable measured in the detection step. In order that such a matrix analysis may be carried out with relatively simple measuring means, at least two detection measurements are carried out in the detection step with different reflection conditions at the interface (5) between the irradiation site (12) and the detection site (13), in each of which the measurement value of the measurement variable is determined.

21 Claims, 3 Drawing Sheets

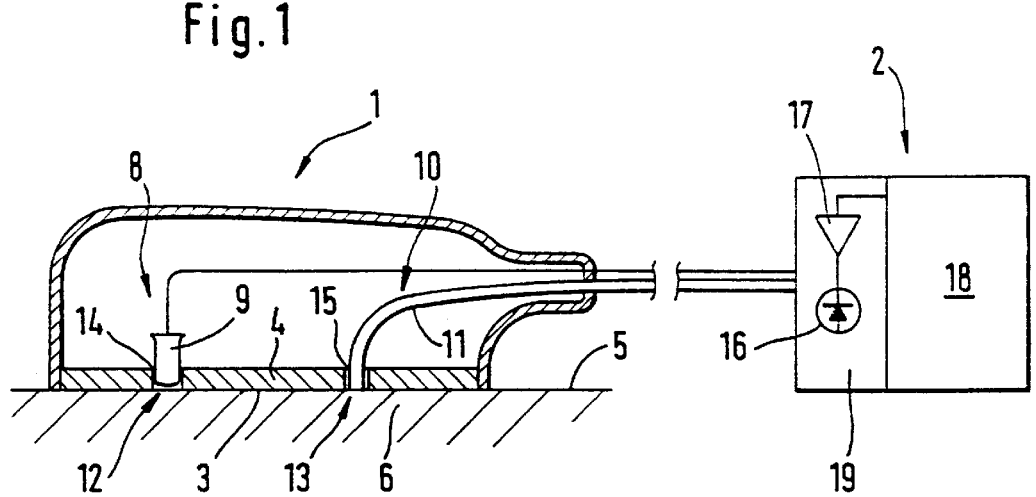
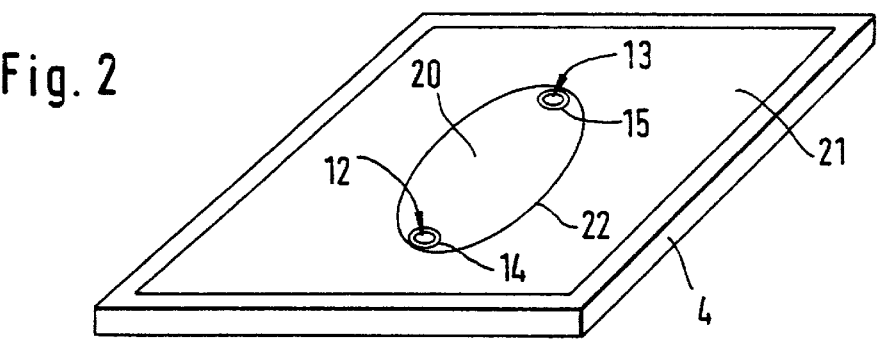
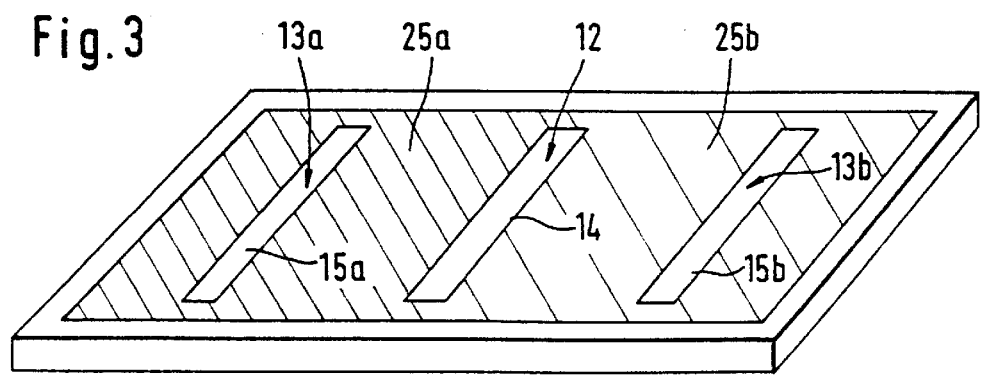

METHOD AND APPARATUS FOR DETERMINING ANALYTICAL DATA CONCERNING THE INSIDE OF A SCATTERING MATRIX

The invention relates to a method and an apparatus for determining analytical data concerning the inside of a scattering matrix, in particular of a biological sample, with the aid of light.

The most important case of the application of the invention is the investigation of biological samples, in particular of the tissue of a living organism. Biological samples are in most cases optically heterogeneous, i.e. they contain a large number of scattering centers at which irradiated light is scattered. This applies to human or animal tissue, in particular skin tissue or subcutaneous fatty tissue, but also to fluid biological samples, such as blood for example, in which the blood corpuscles form scattering centers, or else to milk, in which the scattering centers are formed by emulsified fat droplets. In addition the invention is directed towards scattering matrices in general, in the sense that three-dimensional structures are involved which have such a high density of optical scattering centers that irradiated light is generally scattered many times before it leaves the scattering matrix. Scattering matrices with a mean free path length of the light of less than 5 mm are mainly involved. Non-biological scattering matrices which can be investigated on the basis of the present invention are for example emulsions and dispersions, such as are required for various applications, for example for paints and dyes as well as for surface coatings of plastics materials.

It is also possible for analytical data to be determined by means of the present invention on fluids which do not themselves contain any scattering centers, if the fluids are allowed to flow through a container in which light-scattering particles with preferably known scatter properties are located. In this case the contents of the container (fluid with scattering centers) form a scattering matrix in the sense of the invention. This method can in particular be useful in cases where the desired analytical data on the clear fluid cannot be determined satisfactorily with other methods (for example spectroscopically).

The invention relates to the determination of analytical data which can be determined from the interaction of irradiated light with the matrix ("optical analytical data"). In a "detection step" of such a method, measurements are performed in which light is irradiated with the aid of irradiation means at an irradiation site through an interface bounding the matrix, and at the same time light emerging through the same interface (i.e. "in reflection") is detected at a detection site with the aid of detection means at a predetermined measuring distance from the irradiation site. Such a measuring operation will be referred to below as detection measurement, the irradiated light as primary light and the detected light as secondary light.

In such detection measurements a measurable physical property of the light is determined, which can be described as a "quantifiable parameter" and which will for the sake of simplicity be referred to below as the "measurement variable". The measurement variable is in most cases the intensity of the secondary light, which is frequently measured as a function of the light wavelength. In addition other measurement variables, such as for example the polarizing direction and the degree of polarization of the secondary light (where the primary light is polarized), as well as the phase of the secondary light (where the primary light is irradiated intensity-modulated) are also used to obtain optical analytical data.

From the measurement values of the detection measurements performed in the detection step there can be determined in a subsequent evaluation step, by means of an evaluation algorithm, various analytical data which are dependent on the interaction of the light with the scattering matrix. This refers in particular to parameters which describe quantitatively the optical properties of the scattering matrix, such as the scattering coefficient $\mu_s$, the absorption coefficient $\mu_a$, the anisotropy factor of the scattering g and the refractive index n. Such parameters will be referred to below as "light transport parameters".

In the investigation of biological samples the determination of the concentration of substances contained in the sample, such as for example water, glucose, bilirubin, cholesterol, triglycerides, urea, uric acid, oxyhaemoglobin, haemoglobin or cytochromeoxidase, is of main interest. The concentration of analytes of this kind is as a rule determined invasively, i.e. after removal of a blood sample from the living organism. There has long been a desire to replace this invasive analysis by a pain-free, non-invasive analysis.

There is moreover a close connection between the light transport parameters (in particular $\mu_a$ and $\mu_s$) and the chemical analysis of substances. The latter is based as a rule on spectroscopic principles, i.e. on the investigation of the spectral dependence of the optical absorption. Whereas this is a long established, problem-free method in a clear fluid, there is in biological samples, because of the multiple scattering of the light, the problem that the optical path length of the light in the sample is unknown. If it becomes possible, by means of a suitable measurement method, to determine the optical absorption separately from the scattering (i.e. to separate $\mu_a$ from $\mu_s$), this problem is solved and the known spectroscopic principles can be used for the analysis of numerous substances in biological samples.

Optical analytical data of scattering matrices are therefore of significance for quite different applications. Methods for determining such data will be referred to here collectively as "optical matrix analysis". Optical matrix analysis embraces in particular the investigation of scattering matrices with respect to their light transport parameters and analytical data derivable therefrom.

In connection with the separate determination of analytical data which on the one hand describe the scatter characteristics and on the other the absorption characteristics of light in a scattering medium, the determination of $\mu_a$ and $\mu_s$ from the dependence I(d) of the intensity I of the secondary light on the measuring distance d is discussed. Diffusion theory and numerical-statistical methods (Monte Carlo calculations) form the theoretical basis of this discussion. Reference can be made in this context to the following publications, which are incorporated herein by reference, as non-essential background information:

M. Keijzer et al.: "Optical diffusion in layered media", App. Opt. 27, 1820–1824 (1988);

S. T. Flock et al.: "Monte Carlo modeling of light propagation in highly scattering tissue—I: Model predictions and comparison with diffusion theory", IEEE Trans. Biomed. Eng., 36, 1162–1168 (1989);

T. J. Farrell et al.: "A diffusion theory model of spatially resolved, steady-state diffuse reflectance for the non-invasive determination of tissue optical properties in vivo", Med. Phys., 19, 879–888 (1992).

Although a good agreement of measurement values and theoretical calculations is reported, these methods have not acquired any practical importance, in particular for the determination of analytes in biological samples.

Recently also so-called frequency-domain measuring methods are in discussion. These operate with light modulated at high frequency and therefore call for highly sophisticated measuring equipment.

The invention refers to the problem of improving the optical matrix analysis, in particular as regards the measuring equipment required.

The problem is solved, in a method in which a detection step with detection measurements and an evaluation step of the kind described are carried out, by the fact that in the detection step at least two detection measurements are carried out with different reflection conditions at the interface between the irradiation site and the detection site, in each of which a measurement value of the measurement variable is determined. Each of the quantifiable parameters of the light which were discussed above is considered as a measurement variable, i.e. the intensity of the light as well as the degree of polarization, the polarizing direction and the phase position.

In the context of the invention it has been found that improved optical matrix analysis—in particular an improved separation of the influences of scattering and absorption—is possible if the method is devised in such a way that the reflectivity at the interface between matrix and environment is changed and a new independent externally adjustable variable is thereby introduced. The reflectance behavior can be influenced in various ways. It is only important that photons which on their path from the irradiation site to the detection site arrive at the interface are reflected back into the matrix with differing probability in the two detection measurements. In other words, the possibility that photons leave the matrix at the interface is to be significantly different in the two detection measurements. The light intensity escaping through the interface (with unchanged matrix) is to differ significantly (as a rule by at least 10%) in the two measurements.

The wavelength of the test light can be selected in a wide range between the UV and the infrared (somewhere between 200 nm and 3 $\mu$m). The term light in the sense of the invention is therefore not restricted to the visible spectral region.

By the measuring method according to the invention inter alia the following advantages are achieved:

It is sufficient to determine only the DC intensity of the secondary light. High frequency measurements are not necessary.

Generally relative measurements of the intensity, i.e. measurement of the ratio of the intensity of the secondary light in the two detection measurements, each with different reflectance behavior, are sufficient.

The influences of optical absorption and scattering can be separated.

The dependence of the measured signal on the one hand on the scattering characteristics and on the other on the absorption characteristics of the scattering matrix differs to such an extent that it is in many cases not even necessary to use complicated evaluation methods to calculate the scattering and absorption coefficients.

The invention is directed in particular towards the following aspects of matrix analysis:

Determination of light transport parameters, in particular of an absorption parameter which is a measure of the absorption of the light in the scattering matrix and/or of a scattering parameter which is a measure of the scattering of the light in the scattering matrix. The terms "absorption parameter" and "scattering parameter" refer here to quantities which describe the optical absorption or the light scattering independently of one another. In practice, the absorption is generally described by $\mu_a$ and the scattering by the modified scattering coefficient $\mu_s'=\mu_s(1-g)$, where g is the scattering anisotropy factor.

Determination of the concentration of a substance in the biological sample. Examples of analytes have already been given.

The light transport properties of a scattering matrix are influenced by the substances contained therein in different ways. This applies not only to the optical absorption, the wavelength-dependence of which is conventionally used for the spectroscopic analysis. In many cases the other light transport parameters, in particular the scattering coefficient and the refractive index, are also influenced by the concentration of particular substances in the sample, this phenomenon also being wavelength-dependent. Optical analytical data concerning the light transport parameters in a scattering matrix therefore form a basis for the analysis of substances contained therein.

Changes in concentration lead to characteristic changes in the light transport parameters, which can be determined at one or more wavelengths and be correlated with the concentration of the substance to be analyzed. It is possible to proceed in such a way that one or more of the above-mentioned light transport parameters are explicitly determined and a correlation with the desired analyte concentration by means of a calibration. In many cases it is preferable, however, to make a direct correlation between the measured measurement values of the measurement variable and the analyte concentration (by calibration).

As is known, the reflectance behavior at optical interfaces is dependent on the ratio of the refractive indices at the reflecting interface. If the refractive index na outside is smaller than the refractive index $n_i$ inside the scattering matrix, total reflection is obtained if the angle of incidence is small enough. Biological samples have generally a refractive index of significantly more than 1 (typically of about 1.5). If air is contained in the outside area ($n_a$=1), a large percentage of the photons which reach the interface between irradiation site and detection site are reflected. This reflection is reduced if a substance with a higher refractive index is applied to the interface, for example a gel, whose refractive index corresponds approximately to that of the matrix. In this case photons which reach the interface pass over with high probability into the gel. If the gel (or another substance with a corresponding refractive index) is dark coloured, the photons are absorbed therein, so that they do not pass back into the matrix. A first possibility for influencing the reflectance behavior at the interface therefore is to contact the interface in the intermediate region between irradiation site and detection site during the two detection measurements with substances of different refractive index. This possibility will be referred to as "refractive index embodiment" below.

More practical and therefore preferred, is the possibility to arrange at the interface between irradiation site and detection site reflective surfaces with different reflectivities. For example, in a first detection measurement an optically highly absorbent surface can be arranged (as "contact surface") between the irradiation site and the detection site in contact with the interface of the matrix, while in a second detection measurement a highly reflective contact surface is located between the irradiation site and the detection site ("contact surface embodiment"). Various possibilities for realizing such arrangements will be described in detail by means of the figures.

The invention will be explained in more detail below by means of the figures, where FIG. 1 shows a unit suitable for the invention in a diagrammatic representation partly in cross-section and partly as a block diagram;

FIGS. 2, 3 and 4 show various embodiments of the sample contact plate of a measuring head suitable for the invention;

Figure 6:
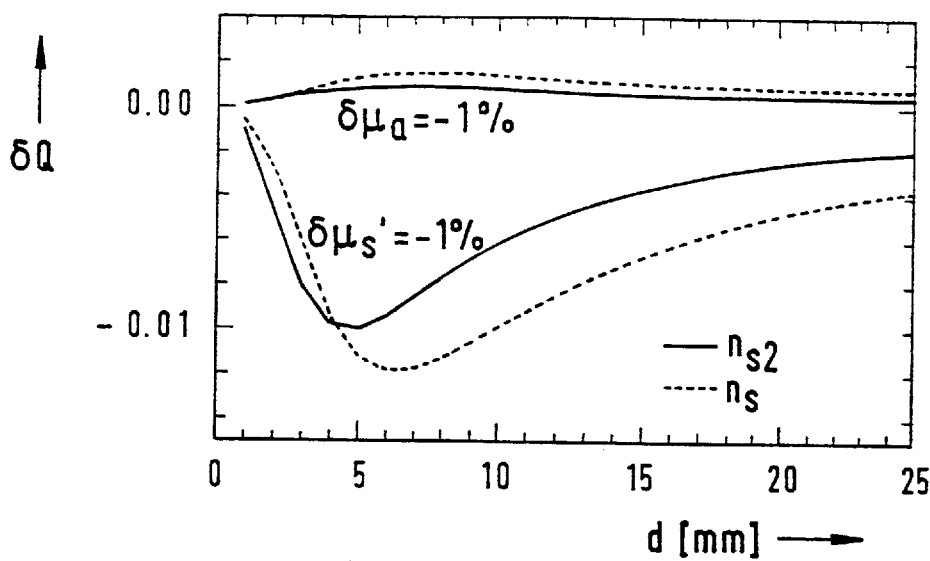
Figure 7:
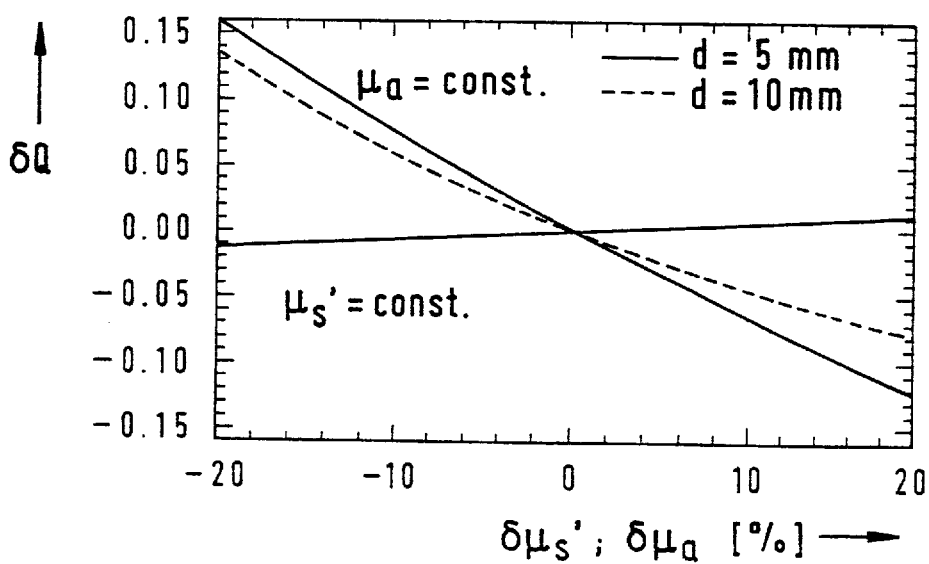

FIG. 6 a graph of the fractional change of Q for each 1% change in the absorption coefficient and the scattering coefficient and FIG. 7 the change of Q as a function of the chain in the absorption coefficient and the scattering coefficient for two different measuring distances.

The apparatus for the optical analysis of scattering matrices which is shown in highly diagrammatic form in FIG. 1 consists essentially of a measuring head 1 and a signal processing and analyzing unit 2.

The measuring head 1 is in contact with an interface 5 of the scattering matrix 6 to be investigated via the sample contact surface 3 of a sample contact plate 4. It contains light irradiation means 8, which in the case shown are formed by a light emitting diode 9 positioned in a recess in the sample contact plate 4 and irradiate light into the matrix 6 through an irradiation opening 14 in the sample contact surface 3, said irradiation opening 14 being formed in this case by the recess in the sample contact plate 4. The detection means 10 include in the embodiment shown a light-conducting fiber 11, which detects the light escaping at a detection site 13 through a detection opening 15 in the sample contact surface 3. The detected light is fed to a photo-receiver 16 (for example an avalanche-type photodiode) arranged in the signal processing unit 19 of the signal processing and analyzing instrument 2. The output signal of the photo-receiver 16 is amplified by an amplifier 17 and coupled to an analyzing unit 18, in which it is processed—preferably digitally by means of a microcomputer—to the desired analytical data.

In the analyzing unit 18 conventional electronic methods are employed for the exact and selective detection of the measurement variable of the light. The use of comparators is conventional for relative measurements. For the elimination of interference the use of pulsed or modulated primary light, in conjunction with a corresponding frequency-selective measuring method (lock-in method), is advantageous.

To this extent the apparatus shown is conventional and therefore does not have to be explained in greater detail. Details on possible designs and different configurations of the measuring head can be taken from the published state of the art. Reference may be made, for example, to WO 94/10901, in which several different arrangements and designs of the light irradiation means and the detection means are described. In particular both the irradiation means and the detection means can be realized in the form of light transmitters or light-sensitive elements integrated directly into the sample contact plate 4 (such as the light transmitter 9 in the present case), or by means of light-conducting fibers which lead the light up to the skin contact plate 4 from a more distant light transmitter or (as in the case shown) transmit it from the detection site 13 to a more distant light receiver.

Figure 4:
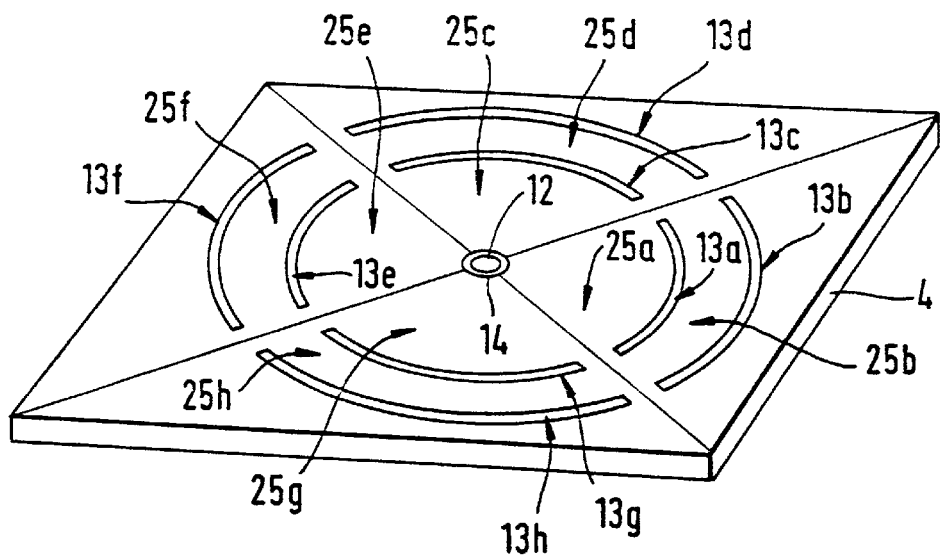

A significant difference compared with the previously known units consists in the fact that the sample contact surface 3 resting against the interface 5 of the matrix 6 is equipped with means by means of which, in at least two detection measurements, different reflection conditions are caused between the respective irradiation site 12 and the respective detection site 13 ("reflection adjustment means"). This can be realized in different embodiments. Sample contact plates 4 representing differing embodiments are shown in FIGS. 2 to 4. The critical factor is the sample contact surface 3 making contact with the matrix 6. The element which carries the sample contact surface 3 does not necessarily have to be formed as a (flat) plate.

In the embodiment shown in FIG. 2 the reflection adjustment means are provided by a sample contact surface 3 with variable reflection properties. An LCD or a ferroelectric display is suitable. These electronic components are commercially available in particular for display purposes, wherein the area of the display is sub-divided into sections whose light reflection properties can be changed by means of electric control signals. In the context of the invention mainly the intermediate area marked as 20 in FIG. 2, namely that between the irradiation opening 14 and the detection opening 15, is to be variable in its reflection properties. The form of the sub-area of the sample contact area 3, which has different reflection properties during the at least two detection measurements, can vary.

The embodiment shown in FIG. 2, with a sample contact surface 3 with adjustable reflection properties, can be used in units (as shown) in which the light is irradiated at only one single irradiation site 12 and detected at only one single detection site 13. This embodiment causes, however, a certain structural complexity and the required electrical activation leads to an (albeit small) energy consumption.

A reduction in this complexity is possible if in the at least two detection measurements of a detection step the light is irradiated at two different irradiation sites and/or detected at two different detection sites, so that different sections of the interface lie between irradiation site and detection site in each case, wherein the reflectance behavior of the contact surface varies in the different sections.

An embodiment of this kind is shown in FIG. 3. In this case the light is irradiated through a light irradiation opening 14 and detected through two detection openings 15a and 15b arranged at the same distance from, but on opposite sides of, the irradiation opening 14. In this case the section of the sample contact area 3 which lies between the irradiation site 12 and the two detection sites 13a and 13b marked by the detection openings 15a and 15b (intermediate area) is different. The intermediate areas 25a, 25b possess strongly different reflection properties, for example the intermediate area 25a can be metallically reflective, so that it acts as a virtually total photon reflector, while the intermediate area 25b is matt black and consequently acts as a photon trap. In such an embodiment the reflection adjustment means are therefore formed by the sections of the sample contact area 3 with different reflectivity in combination with the recesses suitably arranged therein at the irradiation and detection sites.

In the embodiment shown the irradiation sites and detection sites are of longitudinal shape. This permits a good local resolution with relatively high intensity of the light, as is explained in detail in WO 94/10901. Different configurations of the detection sites and the irradiation sites, such as those known from the known state of the art, can be used in the invention.

The embodiment shown in FIG. 3 can also be modified inasmuch as several irradiation sites and one detection site can be used. It is naturally also possible, by means of a multiplicity of irradiation sites and a multiplicity of detection sites, to adjust different light paths in different sections of the matrix to be investigated and in different spatial directions, as is likewise described in WO 94/10901. It is critical in the context of the invention, however, that several detection measurements with different reflection conditions between the respective irradiation site and the respective detection site, but preferably at the same measuring distance, must be possible.

FIG. 4 shows a variant with one irradiation site 12 and in each case two different detection sites 13a,b; 13c,d; 13e,f and 13g,h. In this embodiment two different measuring distances can be set in four spatial directions in each case between the irradiation site and the respective detection site. The intermediate areas also in this case have different reflectivity, wherein preferably opposite intermediate regions (e.g. 25a, 25e and 25c, 25g) have identical reflection properties.

Figure 5:
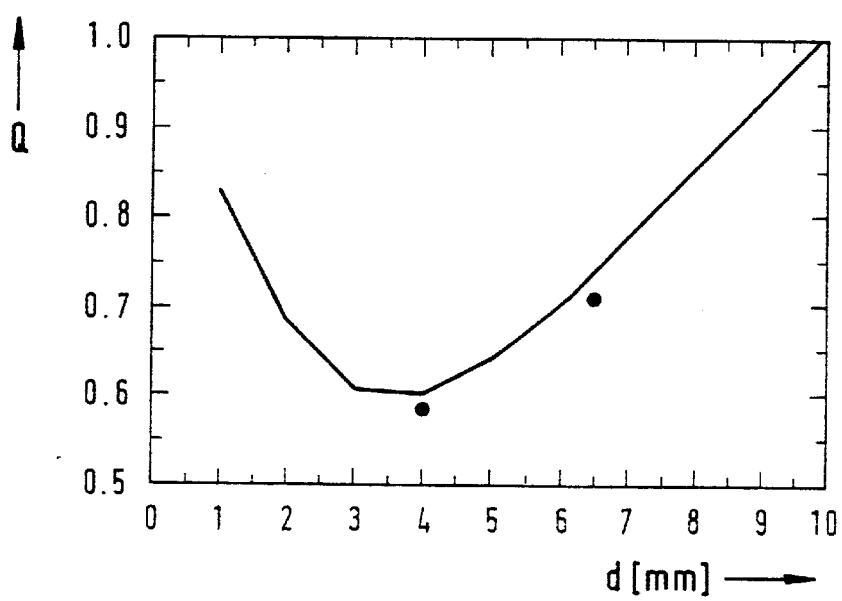
FIG. 5 shows a graph of the dependence on the measuring distance of the quotient Q of the intensity of the secondary light during detection measurements with two different reflection conditions.

FIG. 5 shows experimental results which were obtained with an experimental model of a scattering matrix, the optical properties of which correspond essentially to those of human skin tissue. It consisted of a cuboid with the dimensions 8 cm×8 cm×20 cm, an absorption index of $\mu_a$=0.02 mm$^{-1}$, a modified scattering index of $\mu_s'$=0.9 mm$^{-1}$ and a refractive index on the inside of the matrix of $n_i$=1.56 at a wavelength of light of L=780 nm. The light was irradiated and detected at the interface of the experimental model of two optical fibers with a core diameter of 100 μm, which were positioned at fixed measuring distances of d=4 mm and d=6.5 mm.

The reflection properties in the intermediate area between irradiation site and detection site were varied by changing the refractive index $n_a$. A first series of measurements was carried out with air ($n_a$=1) in the outside area at the interface between the irradiation site and the detection site. In a second series of detection measurements the interface was covered with a gel with a refractive index of $n_a$=1.46. It was mixed with a black colour in order to absorb practically all of the light which had penetrated into the gel.

The refractive index ratio $n_s$=$n_i$/$n_a$ determines in known manner the reflection properties at the interface, which are also referred to as boundary conditions in technical language. With the experimental conditions described two different boundary conditions $n_{s1}$=1.56 and $n_{s2}$=1.07 can be set. The term $n_s$ will be used throughout below for the reflection properties (boundary conditions) in the intermediate area between irradiation site and detection site, i.e. irrespective of whether the various reflection conditions are realized (as in the experimental model described) by the refractive index embodiment or, as in FIGS. 2 to 4, by the contact surface embodiment.

In the graph of FIG. 5 there is plotted on the ordinate the quotient Q of the intensity I of the secondary light for detection measurements with two different boundary conditions $n_s$:

$$Q(n_{s1}, n_{s2}) = I(n_{s1})/I(n_{s2})$$

This measurement variable is shown in its dependence on the measuring distance d, wherein the experimental results are marked as dots.

The continuous curve represents calculations obtained by diffusion theory (equation (18) of the above-mentioned article by T. J. Farrell et al.). This describes the dependence of the diffuse reflection on the measuring distance d under given optical conditions R(d)|$\mu_a, \mu_s', n_s$. From this one gets $$Q(d)|\mu_a, \mu_s', n_{s1}, n_{s2} = \frac{R(d)|\mu_a, \mu_s', n_{s1}}{R(d)|\mu_a, \mu_s', n_{s2}}$$

An astonishingly good agreement between experiment and theory is obtained, in particular considering that no normalization of any kind was made. The experimental dots were simply corrected by a factor of F=2.43, in order to allow for the fact that no gel was applied at the contact surface of the light-conducting fibers with the interface and hence also no change in the refractive index was present in this partial area of the interface, whereas in Farrell's theory a uniform refractive index across the entire interface is assumed. The factor F=S($n_{s1}$)/S($n_{s2}$) is obtained from the ratio—determined by $n_{s1}$ and $n_{s2}$—of the segments S of the matrix, from which segments light can emerge and be collected by the detector fiber: S($n_2$)≈3−2cosθ−cos$^2$θ, where θ≈sin$^{-1}$(1/$n_s$).

The light transport parameters and other optical analytical data associated with them can be determined in various ways on the basis of the explanations given here and the experimental results shown.

Preferably in the evaluation step first a ratio Q of intensity measurement values for the at least two measurements with different reflection conditions is calculated. If Q, as shown in FIG. 5, is determined as a function of the measuring distance d for several measuring distances, the coefficients $\mu_a$ and $\mu_s'$ can be determined separately by fitting the above-mentioned diffusion theory equations to the experimental results. Alternatively it is possible to measure for a measuring distance d a plurality of relationships $Q_i$ for different $n_{si}$'s. This also allows separation of $\mu_a$ and $\mu_s'$. In general at least two detection measurements with different boundary surface conditions nsi are preferably carried out for at least two measuring distances $d_i$ in each case.

As already mentioned, the algorithm for determining the desired analytical data on the basis of the measurement variable measured in the detection step can also be purely empirical. An increasing number of numerical correlation methods have recently been used in chemical analysis, in order to form a correlation between the measurement variables (input variables) and the analytical data sought (output variables) based on a calibration with samples for which the data to be analyzed are known. The latter include iterative methods for the optimal description of the relationship of input variables and output variables, as well as multilinear and non-linear algorithms. Neural networks are also used for this purpose.

In the present invention the skilled person can use such numerical methods on the basis of the explanations given here, wherein a relationship Q does not necessarily have to be formed. Instead, measurement values I($n_s$)|$d_i$ of the measurement variable which have been measured as a function of the boundary conditions can be used directly as input variables of an evaluation algorithm. This can take place for one measuring distance d or for several measuring distances $d_i$. In the case of only one measuring distance d preferably at least three values of I are measured for three different values of $n_s$.

FIG. 6 shows a graph of the fractional change δQ of Q for a one per cent change in the absorption coefficient and in the scattering coefficient. The curves were calculated on the basis of the above-mentioned equation of diffusion theory, wherein $\mu_a$=0.01 mm$^{-1}$ and $\mu_s'$=1 mm$^{-1}$ have been assumed for the optical properties. Three different values $n_s$=1.0; 1.4 and 1.6 were used for the boundary conditions.

In FIG. 6 the change δQ ($\mu_a, \mu_s'$) per fractional change δ$\mu_a$=−1% or δ$\mu_s'$=−1% is plotted as a function of the distance d. It is seen that Q shows a very much higher dependence on the modified scattering coefficient $\mu_s'$ than on the absorption coefficient $\mu_a$. Particularly in the central range of the measuring distances between about 2 mm and about 12 to 15 mm the sensitivity of the measuring method for changes in the scattering coefficient is particularly high, i.e. the scattering coefficient can be determined with particularly good accuracy in this preferred measuring distance range.

On the basis of these results the present invention is in particular suitable for the quantitative analysis of the optical scattering properties of biological samples and other scattering matrices. According to WO 94/10901 the scattering properties of the multiple scattering of light in such samples is dependent to an astonishingly high extent on the concentration of glucose in the sample. The present invention is therefore suitable in particular for the analysis of glucose with the use of the principles explained in WO 94/10901.

In order to permit a better comparison of the dependence of Q on changes in the scattering and absorption, Q was calculated as a function of $\mu_s'$ and $\mu_a$ for measuring distances d=5 mm and d=10 mm. This dependence is shown in FIG. 7 (for $n_{s2}$=1.4, $n_{s1}$=1.0) in a variation range of $\mu_s'$ and $\mu_a$ of ±20%. The change as a function of $\mu_s'$ is ten to fifteen times as high as the change as a function of the absorption. At the same time it is remarkable that the dependence coincides to a large extent for the two measuring distances measured.

We claim:

1. A method for determining analytical data regarding a light scattering matrix, said method comprising the steps of:
   detecting secondary light by irradiating light into the scattering matrix as primary light at an irradiation site through an interface bounding the scattering matrix, and detecting light emerging out of the scattering matrix through the interface, said emerging light being detected as secondary light at a detection site which is located at a predetermined measuring distance from the irradiation site;
   determining a measurement value of a measurable physical property of the secondary light, said measurable physical property varying due to an interaction of the primary light with the scattering matrix;
   evaluating the measurement value as a measure of the analytical data to be determined, the analytical data being determined based upon a measurement value of the measurement variable,
   wherein at least two of said detecting steps are carried out under different reflection conditions at the interface between the irradiation site and the detection site, and measurement values determined in said at least two detection steps are evaluated in said evaluation step to determine said analytical data.

2. A method according to claim 1, wherein the measurement variable is an intensity of the secondary light at the detection site.

3. A method according to claim 1, wherein said evaluation step comprises a step of forming a ratio of at least two measurement values formed during the at least two detecting steps.

4. A method according to claim 1, wherein said at least two detecting steps are performed with different measuring distances between the irradiation site and the detection site.

5. A method according to claim 1, wherein the at least two detecting steps are performed with a same measuring distance between the irradiation site and the detection site.

6. A method according to claim 1, wherein said at least two detecting steps are performed with reflective surfaces having differing reflectivities arranged between the respective irradiation site and the detection site at the interface bounding the biological sample.

7. A method according to claim 6, wherein the different reflectivities of the at least two detecting steps are formed by changing the reflectivity of a reflecting surface.

8. A method according to claim 6, wherein one of a first irradiation site and a first detection site in a first of said at least two detecting steps is different than one of a second irradiation site and a second detection site of a second of said at least two detecting steps, so that different sections of the interface are disposed between the respective irradiation and detection sites in said first and second detection steps and said different sections have respective reflectivities of different values.

9. A method according to claim 1, wherein the analytical data includes an absorption parameter which corresponds to a measure of the optical absorption of the primary light in the scattering matrix.

10. A method according to claim 1, wherein the analytical data includes a scattering parameter which corresponds to a scattering of the primary light in the scattering matrix.

11. A method according to claim 10, wherein the light scattering matrix is a biological sample.

12. A method according to claim 11, wherein the analytical data includes a concentration of an analyte in the biological sample.

13. A method according to claim 12, wherein a concentration of an analyte in the biological sample is determined based upon the absorption parameter.

14. A method according to claim 12, wherein a concentration of an analyte in the biological sample is determined based upon the scattering parameter.

15. A method according to claim 1, wherein the biological sample comprises skin tissue.

16. A method according to claim 1, wherein the biological sample comprises subcutaneous fatty tissue.

17. A method according to claim 1, wherein the biological sample comprises sclerae tissue.

18. An apparatus for determining analytical data of a light scattering matrix, said apparatus comprising:
   a measuring head, said measuring head including a sample contact surface for contacting an interface of the biological sample;
   light irradiation means disposed in said measuring head for irradiating light into the biological sample at an irradiation site through an irradiation opening in the sample contact surface,
   detection means connected to said measuring head for detecting secondary light emerging from the scattering matrix at a detection site through a detection opening in the sample contact surface;
   evaluation means connected to said light irradiation means and said detection means for determining analytical data based upon the primary light and the secondary light,
   wherein said sample contact surface includes reflection adjustment means wherein different reflection conditions can be provided in at least two detection measurements.

19. An apparatus according to claim 18, wherein said reflection adjustment means comprises a liquid crystal display.

20. An apparatus according to claim 18, wherein said sample contact surface includes at least two irradiation openings, such that a first section of said sample contact surface is disposed between a first of said at least two irradiation openings and the detection opening, and a second section of said sample contact surface is diposed between a second of said at least two irradiation openings and the detection opening, said first section and said second section having respective reflectivities of different values.

21. An apparatus according to claim 18, wherein said sample contact surface includes at least two detection openings wherein a first section of the sample contact surface is disposed between the irradiation opening and a first of the at least two detection openings, and a second section of the sample contact surface is disposed between the irradiation opening and a second of the at least two detection openings, and wherein the first section and the second section have respective reflectivities of different values.

\* \* \* \* \*